United States Patent [19]

Tokuhiro et al.

[11] Patent Number: 5,030,253
[45] Date of Patent: Jul. 9, 1991

[54] FRAGRANT AIR SUPPLYING METHOD AND SUPPLYING SYSTEM

[75] Inventors: Tomoya Tokuhiro; Hisato Yano; Tsuyoshi Horiyama; Norihiro Yamaguchi; Hiroaki Watanabe; Shusa Hashimoto, all of Tokyo, Japan

[73] Assignee: Shimizu Construction Co., Ltd., Tokyo, Japan

[21] Appl. No.: 610,348

[22] Filed: Oct. 31, 1990

Related U.S. Application Data

[63] Continuation of Ser. No. 358,936, May 26, 1989, abandoned.

[30] Foreign Application Priority Data

May 31, 1988 [JP] Japan ................... 63-133220

[51] Int. Cl.$^5$ .............................. B01F 3/04
[52] U.S. Cl. ........................... 55/89; 55/90; 55/257.5; 261/81; 261/DIG. 48; 261/DIG. 65; 261/78.2; 422/124
[58] Field of Search .......... 261/DIG. 65, DIG. 48, 261/81, 78.2; 422/124; 55/257.5, 89, 90

[56] References Cited

U.S. PATENT DOCUMENTS

| 422,202 | 2/1890 | Furney | 55/257.5 |
|---|---|---|---|
| 1,508,399 | 9/1924 | Kohut | 55/257.5 |
| 2,686,944 | 8/1954 | Gubelin | 261/DIG. 65 |
| 3,298,674 | 1/1967 | Gilbertson | 422/124 |
| 3,392,916 | 7/1968 | Engstrom et al. | 261/DIG. 48 |
| 3,490,436 | 1/1970 | Hart | 422/124 |
| 3,711,023 | 1/1973 | Smith | 239/54 |
| 3,744,722 | 7/1973 | Burns | 261/DIG. 65 |
| 4,109,863 | 8/1978 | Olson et al. | 261/DIG. 48 |
| 4,116,387 | 9/1978 | Kremer, Jr. et al. | 261/DIG. 65 |
| 4,303,617 | 12/1981 | Bryson | 422/124 |
| 4,601,886 | 7/1986 | Hudgins | 422/116 |
| 4,695,434 | 9/1987 | Spector | 422/124 |

FOREIGN PATENT DOCUMENTS

| 0004039 | 9/1979 | European Pat. Off. . |
|---|---|---|
| 0295129 | 12/1988 | European Pat. Off. . |
| 62-49138 | 3/1987 | Japan . |
| 63-160660 | 7/1988 | Japan . |
| 237992 | of 1925 | United Kingdom ........ 55/257.5 |

*Primary Examiner*—Tim Miles
*Attorney, Agent, or Firm*—Darby & Darby

[57] ABSTRACT

The present invention relates to a fragrant air supplying method, supplying apparatus, and a building having a fragrant air supplying system for supplying fragrant air to the rooms. A fragrant-material supplying means supplies fragrant material to a mist-generating means to generate mist either by blowing air or by vibration produced by an ultrasonic-oscillating means. The mist is blown to a surface portion formed at the end of a fragrant-air separating means which separates evaporated fragrant air from mist. The fragrant air is then introduced into holes formed in a fragrant-air discharging means, in which the place of holes are offset from the surface portion toward the downstream of the fragrant air. The fragrant air is then blown into a distributing passage from the fragrant-air discharging means to mix the fragrant air with conditioned-air supplied by an air-supplying means. This makes fragrance-mixed air for distributing to a predetermined space or rooms for the physical and mental activation of the human body.

20 Claims, 4 Drawing Sheets

FRAGRANT AIR SUPPLYING METHOD AND SUPPLYING SYSTEM

This is a continuation of application Ser. No. 358,936, filed May 26, 1989, now abandoned.

BACKGROUND OF THE INVENTION

1. Field of the Invention

The present invention relates to a fragrant air supplying system, and more particularly to a fragrant air supplying method, supplying apparatus which are used for diffusing fragrant air into a predetermined space, and a building having a fragrant-air supplying system.

2. Prior Art

Recently, it is increasing interest to improve our living environment by using fragrance. It has been thought that, for example, fragrance can be used not only for getting rid of odors such as tobacco, but for having a physiological and psychological beneficial effect on the human body.

The physiological and psychological influence of conventional fragrant materials on the human body has been experientially known and used in medical treatment known a "aromatherapy". It has been proved that several fragrant materials have the effect of enhancement of awareness, tranquilizing, and changing the physiological condition of the human body by examining contrac negative variation (CNV) or the like of encephalon brain waves. Furthermore, in the case where fragrant material such as lemon is mixed with the air and evaporated into air in a conference room, a key-operator room, or the like, it has also been proved that the fragrant material facilitates transactions at the conference, and decreases the error rate of key operation.

Accordingly, there are several types of fragrant materials; a lemon type fragrant material enhances the awareness and stimulates the circulatory system of the body; a lavender type fragrant material tranquilizes and relieves stress, anxiety, depression, or the like; and a rosemary type fragrant material increases appetite, causes relaxation, and the like; and a phytoncide cleans the air, killing harmful bacteria and viruses.

In previous practice, the fragrant material is impregnated into a porou ceramic unit to evaporate the fragrant material into the air in a room. This unit is placed in the room to evaporate the fragrant material into the air by natural evaporation.

However, in the case where the fragrant material is evaporated into the air of the room by the above-described means, the period of effectiveness of the fragrance is short and the density thereof cannot be controlled. In addition, since the evaporated fragrance air is not uniformly spread in the room, the effect of the fragrance, cannot be well-controlled.

Furthermore, in the case of evaporating fragrance into a large space, a great volume of fragrant material should be impregnated in a porous ceramic supplier.

Fragrant materials may contain a few to several hundred components, the each of which is quite different. Thus, when a multiple component fragrant material is evaporated into the air under natural conditions the readily-evaporated fragrant material is evaporated into the air first. Thus, it is difficult to evaporate specific ingredients of fragrant material in the proper proportions. In addition, the properties of fragrant materials may change periodically into a different fragrance after evaporating into the air.

OBJECT AND SUMMARY OF THE INVENTION

Accordingly, it is an object of the present invention to provide a fragrant-air supplying method which can maintain a predetermined concentration of fragrance in a predetermined space by forcibly evaporating fragrant material.

Another object of the present invention is to provide a fragrant-air supplying apparatus which can adjust the concentration of fragrance, select the desired type of fragrance, and supply an intermittent or continuous quantity of fragrant air to a predetermined space.

Another object of the present invention is to provide a building having a fragrant-air supplying system which can equally distribute fragrant air of the desired type of into rooms.

In a first aspect of this invention, there is provided a method for supplying fragrant air, the method comprising the steps of: spreading at least one fragrant material in the air to evaporate the fragrant material in the air; separating the mist composed of the fragrant material from the air containing the evaporated fragrant material; and providing a predetermined space with the air containing the evaporated fragrant material.

In a second aspect of this invention, there is provided an apparatus for supplying fragrant air, the apparatus comprising: retaining means for retaining at least one fragrant material; spreading means for spreading the fragrant material in small particles into the air; separation means for separating a mist made of the fragrant material from the gaseous rest, the separation means having a target means wherea the mixture of the mist and the air containing the fragrant material is blown and the mist coheres on the surface thereof.

In a third aspect of this invention, there is provided a building having an apparatus for supplying fragrant air, wherein the building having an apparatus for supplying fragrant air comprises a fragrant- material supplying means; a mist-generating means for mixing a predetermined amount of fragrant material supplied from the fragrant-material supplying means with air which is supplied by externally to compose the mist; fragrant-air separating means comprises mist-collided means, fragrant-air introducing means, and fragrant-air discharging means, in which the mist-collided means is struck by mist generated from the mist-generating means to separate fragrant air from the mist, the fragrantair introducing means introduces fragrant air, and the fragrant-air discharging means discharges fragrant air from the fragrant-air introducing means; and air-supplying means for mixing fragrant air discharged from the fragrant-air discharging means with conditioned-air supplied from an air conditioner to make fragrance-mixed air, and supplying the fragrance-mixed air to room in the building through distributing passages.

DESCRIPTION OF PREFERRED EMBODIMENT OF THE INVENTION

Hereinafter, an embodiment of the present invention is described by reference to drawings.

Figure 1:
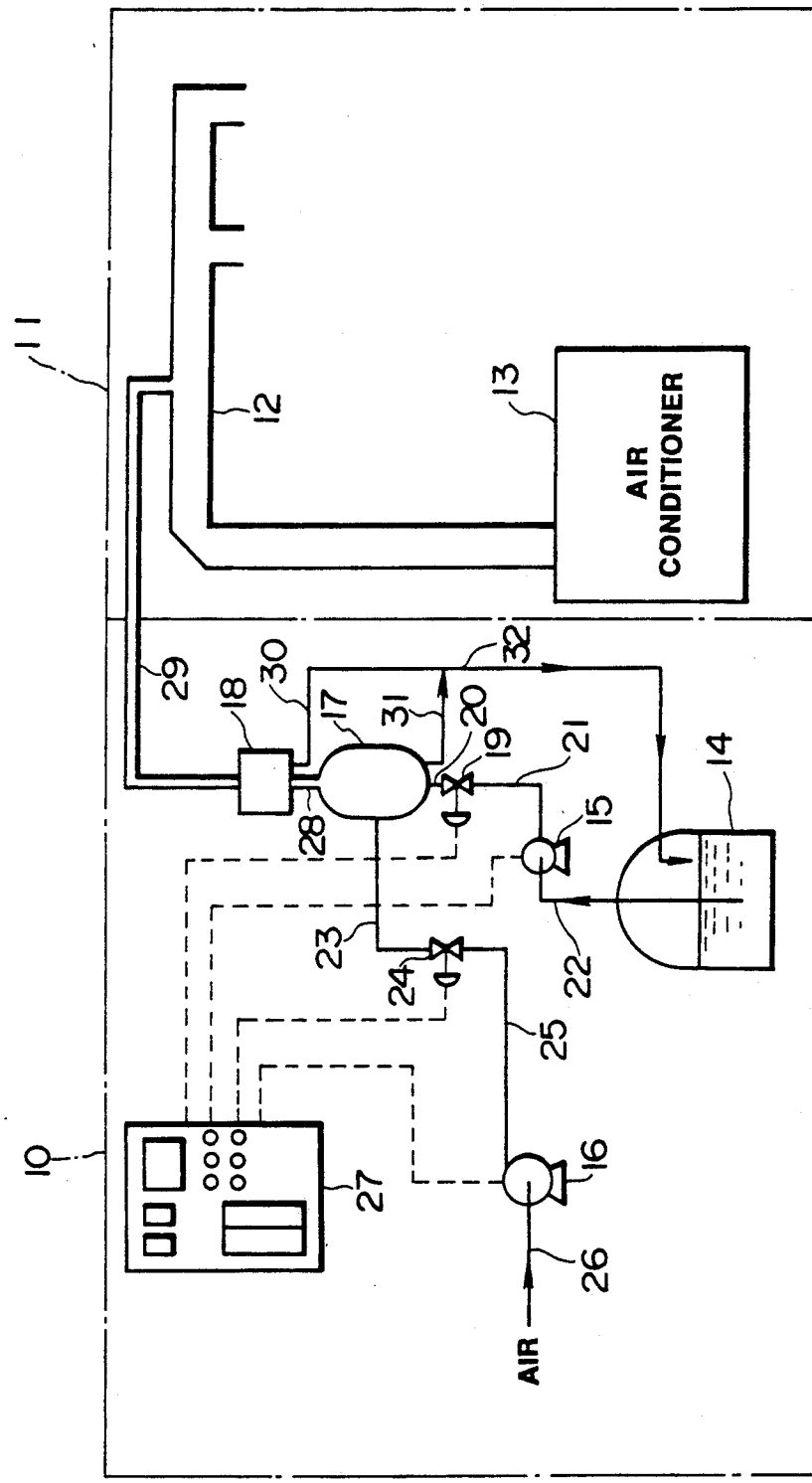
FIG. 1 is a diagram illustrating an embodiment of the fragrant-air supplying system of the present invention.

FIG. 1 shows a fragrant-air supplying system. The fragrant-air supplying system comprises fragrant-air supplying apparatus 10 and air-conditioning facility 11. This fragrant-air supplying system supplies fragrance-mixed air to a room by mixing fragrant air with conditioned-air. The conditioned-air is supplied by air-conditioning facility 11 which includes main air duct 12 extending from air conditioner 13. Fragrant-air supplying apparatus 10 comprises fragrant liquid reservoir 14, fragrance-supplying pump 15, blower 16, fragrance evaporator 17, and impactor 18.

In fragrance evaporator 17, the outlet of flow-regulating valve 19 is installed at the bottom of fragrance evaporator 17 through a pipe 20 and the inlet thereof is connected to the discharge side of fragrance-supplying pump 15 through pipe 21. The intake side of fragrance-supplying pump 15 has a pipe 22 which extends into fragrant liquid reservoir 14 and the end portion of pipe 22 is submerged in fragrant liquid therein.

In addition, one end of pipe 23 is connected to the lateral side of fragrance evaporator 17 and the other end is connected to the outlet of flow-regulating valve 24. The inlet of flow-regulating valve 24 has pipe 25, the end of which is connected to the discharge side of blower 16. The intake side of blower 16 has a pipe 26 connected to a compressor which is not shown in the drawing. The details of fragrance evaporator 17 are described later.

The above-described fragrance-supplying pump 15, flow-regulating valve 19, blower 16, and flow-regulating valve 24 are electrically connected to controller 27 to control in accordance with a control sequence incorporated therein. Accordingly, the operation of fragrance-supplying pump 15 pumps fragrant liquid up to fragrance evaporator 17 and a predetermined quantity of fragrant liquid, regulated by flow-regulating valve 19, is supplied into fragrance evaporator 17. On the other hand, operation of blower 16 supplies compressed air into fragrance evaporator 17 and a predetermined quantity of air, regulated by flow-regulating valve 24, is supplied to fragrance evaporator 17.

In the top of fragrance evaporator 17 mist-discharging extension 28 is extended and connected to the bottom of impactor 18, the top of which has duct-connecting pipe 29. The other end of duct-connecting pipe 29 is connected to main air duct 12 to blow fragrant air thereinto The details of impactor 18 ar described later. Main air duct 12 is used for distributing conditioned-air supplied by air conditioner 13 to the room.

In addition pipe 30 is extended from the bottom of impactor 18 and pipe 31 being also extended from the bottom of fragrance evaporator 17. Pipe 31 is connected by T junction to pipe 32, end portion of which is penetrated into the fragrant liquid reservoir 14 to return the dripping fragrant liquid thereto.

Figure 2:
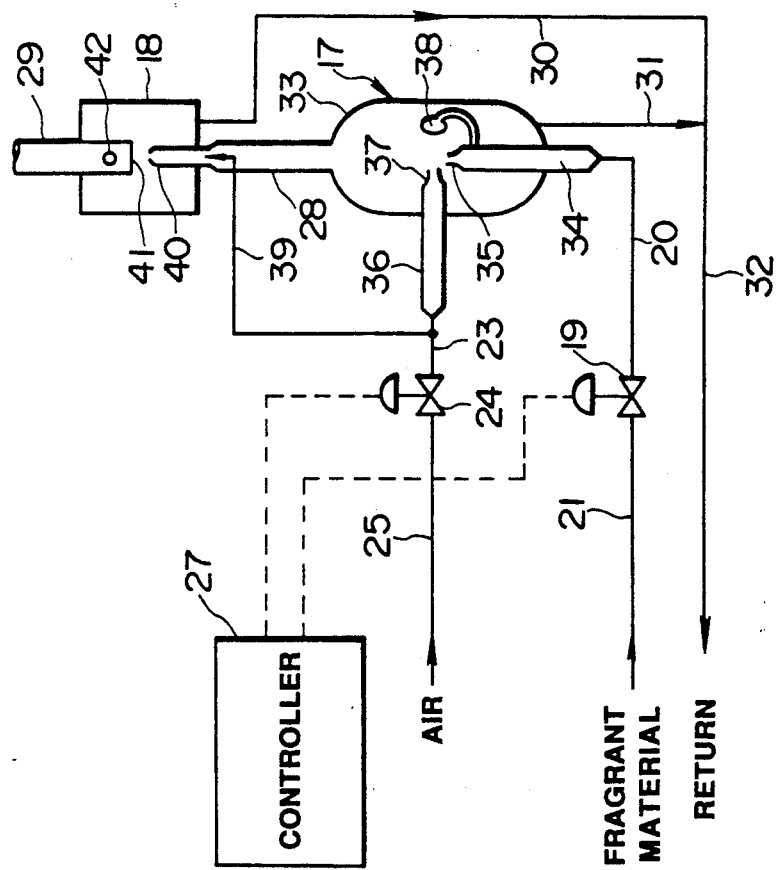
FIG. 2 is a diagram illustrating an embodiment of the fragrant-material supplying equipment.

Next, a detailed description of the fragrance evaporator 17 is described by reference to FIG. 2. Fragrance evaporator 17 comprises vessel portion 33 and the above-described mist-discharging extension 28. At the bottom of vessel portion 33, fragrance-accumulating pipe 34 penetrates into vessel portion 33 and the middle portion thereof is fixed to the wall of vessel portion 33. Fragrance nozzle 35 formed at one end of the fragrance-accumulating pipe 34 is open in the vertical direction along the longitudinal direction of vessel portion 33, the other end of fragrance-accumulating pipe 34 being connected to the end of pipe 20 which extends from flow-regulating valve 19. At the lateral side of vessel portion 33, air-accumulating pipe 36 extends into vessel portion 33 and the middle portion thereof is fixed at the wall of vessel portion 33. Air nozzle 37 formed at one end of air-accumulating pipe 36 is open in the horizontal direction in response to the longitudinal direction of vessel portion 33, the other end of air-accumulating pipe 36 being connected to the end of pipe 23 which extends from flow-regulating valve 24. In addition, air buffer 38 is fixed to fragrance-accumulating pipe 34 so that the face of air buffer 38 faces to air nozzle 37 to mix air with fragrant liquid.

Furthermore, one end of pipe 39 is connected at pipe 23 by a T junction and the other end thereof being connected to the end portion of mist-discharging extension 28 to blow compressed air toward impactor 18. Accordingly, by squirting fragrant liquid from fragrant nozzle 35 vertically, with compressed air blowing horizontally against the squirting fragrant liquid mixes the compressed air with the fragrant liquid. This mixture is composed of a mist which is blown toward the end portion of mist-discharging extension 28. The compressed air also supplied through pipe 39 and blown toward impactor 18, assists in blowing the mist into impactor 18.

Impactor 18 is formed by a box or the like. The end portion of mist-discharging extension 28 extends into the bottom of impactor 18 and is fixed at the wall of impactor 18. Mist nozzle 40 is formed at the end of mist-discharging extension 28 to blow the mist. The previously described duct-connecting pipe 29 extends into the top of impactor 18 and is fixed at the wall thereof. End face 41 is formed at the end of duct-connecting pipe 29 to be struck by the flowing mist, and incoming hole 42 being open at the lateral side of duct-connecting pipe 29 where it is placed slightly above end face 41 to introduce fragrant air. That is, the mist particles are removed at end face 41 and the fragrance liquid being readily evaporated into compressed air to make fragrant air. This fragrant air flows into incoming hole 42, duct-connecting pipe 29, and then into main air duct 12 to mix with conditioned-air to produce fragrance-mixed air. When the mist strikes at end face 41, drops of fragrant liquid which are not evaporated into the compressed air are produced. These drops of fragrant liquid are returned to fragrant liquid reservoir 14 through pipe 32.

Figure 3:
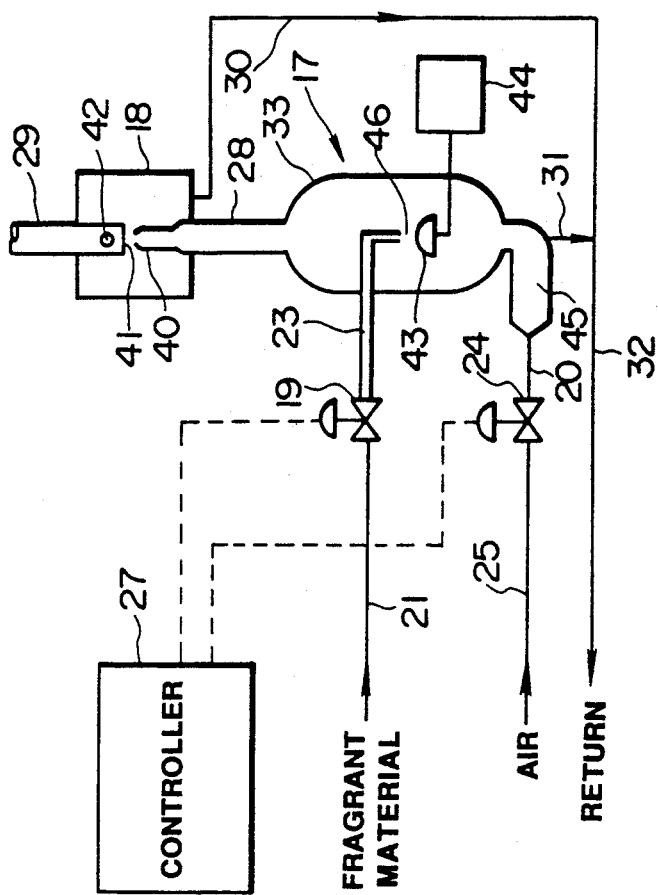
FIG. 3 is a diagram illustrating another embodiment of the fragrant-material supplying equipment.

FIG. 3 shows another embodiment of fragrance evaporator 17. In this fragrance evaporator 17, the feature of the construction is that vibrator 43 connected to ultrasonic oscillator 44 is used for making mist. Vessel portion 33 is constructed having air-receiving extension 45 to receive air so that the received air spreads under vibrator 43. The opening 46 in pipe 23 is placed above vibrator 43 to feed fragrant liquid thereto. Ultrasonic oscillator 44 is powered by a few to several tens of watts and being able to generate frequencies from a few tens of kHz to several MHz to vibrate vibrator 43. Accordingly, by feeding fragrant liquid to vibrator 43, vibration of vibrator 43 makes a mist which is mixed fragrant liquid with air supplied fro air-receiving extension 45. This mist is blown to end face 41 in impactor 18 through mist-discharging extension 28. Another construction of this type of fragrance evaporator 17 is similar to the others shown in FIG. 2 which has been already described. Therefore, the same reference numerals are designated for the similar construction and a detailed description being omitted.

In this embodiment, the particle size of the mist is much smaller than that other which is produced by fragrance evaporator 17 in the first embodiment. Thus, the volume of dripping fragrant liquid is less. In other words, a larger quantity of fragrant liquid can be readily evaporated into the air supplied from air-receiving extension 45.

Figure 4:
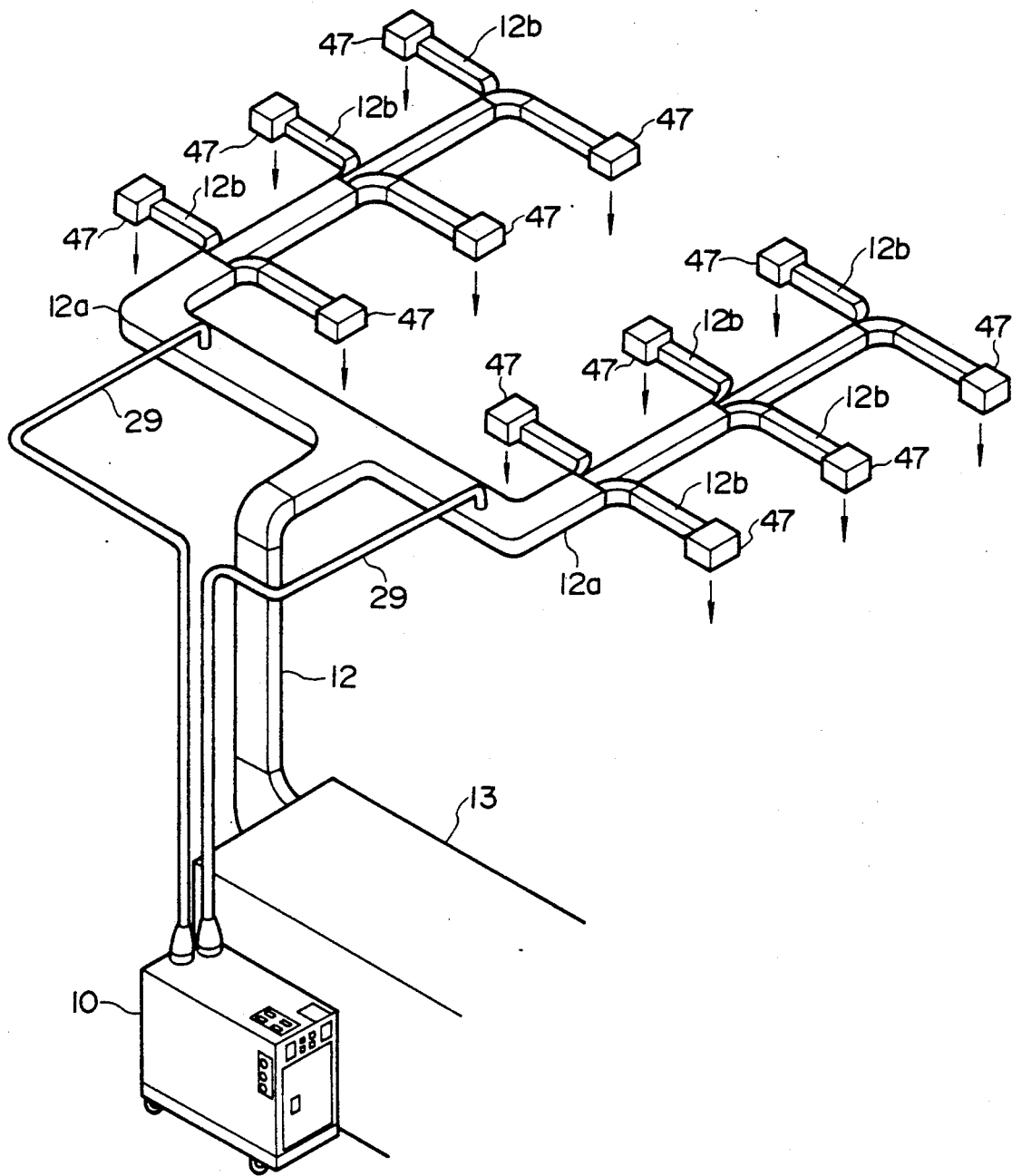
FIG. 4 is a perspective view of the air-supplying system.

FIG. 4 shows an example of a fragrant-air supplying system in a building. Fragrant air supplying apparatus 10 is installed beside air conditioner 13 and two duct-connecting pipes 29 being extended therefrom, then connected to two air ducts $12_a$, respectively. Each air duct 12*a* being diverged to plural branch ducts $12_b$, each of which is extended to the room in the building. Each end of branch ducts $12_b$ is connected to louver 47 to blow the fragrance-mixed air into the room in the building. Thus, the fragrance-mixed air is distributed evenly throughout the room, so that the concentration of fragrance is uniform.

Figure 5:
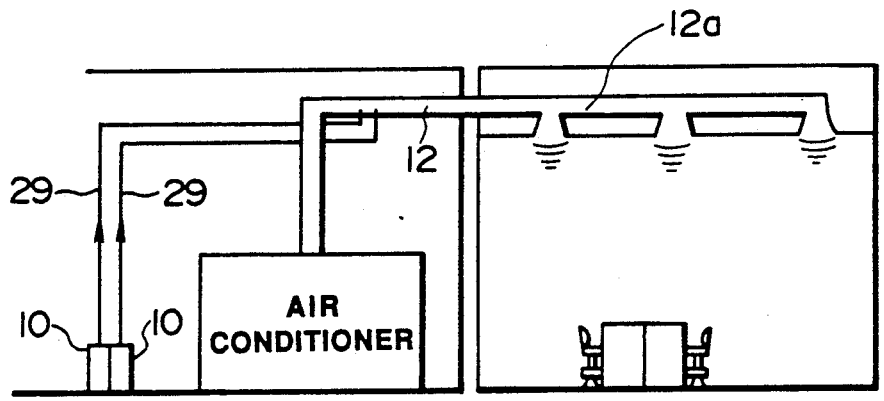
FIG. 5 is a side view illustrating an example layout of the fragrant-air supplying system.

FIG. 5 shows another example of a fragrant-air supplying system in a building. In this case two fragrant air supplying apparatuses 10 intermittently supply two different types of fragrant air to the room.

In another example of a fragrant-air supplying system shown in FIG. 5, two fragrant air supplying apparatuses 10 intermittently or continuously supply two different types of fragrant air to each room through air ducts 12*a* which are arranged for two separate rooms, respectively.

In still another example of a fragrant-air supplying system in the building which is not shown in the drawing, more than three fragrant-air supplying apparatuses 10 can be installed in cooperation with air conditioner 13 to supply more than three types of fragrant air to a room or rooms.

Accordingly, in the case where more than two types of fragrant air are supplied to a room or rooms, a desirable fragrance-mixed air condition can be predetermined and set in controller 27 such as the use of fragrance type, concentration of fragrance-mixing air, and time interval for blowing fragrance-mixing air.

Figure 6:
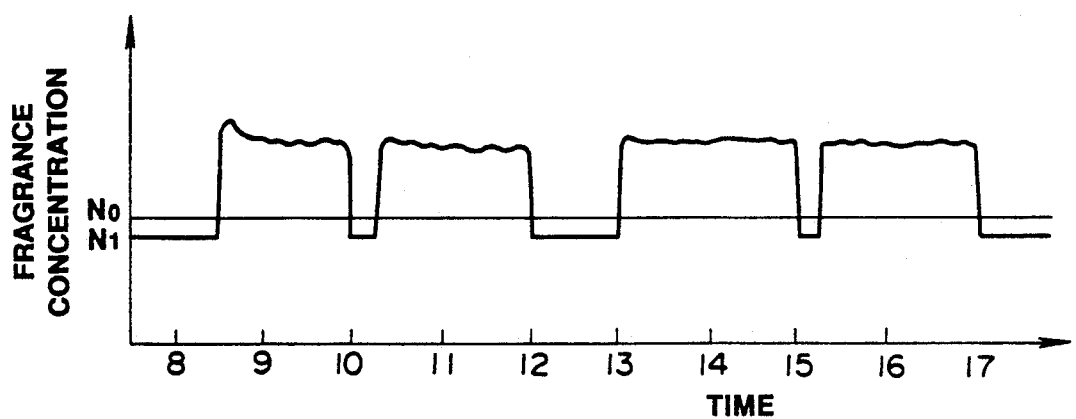
FIG. 6 and 7 are graphs showing the relationship between time and the concentration of fragrance in the experimental results.
Figure 7:
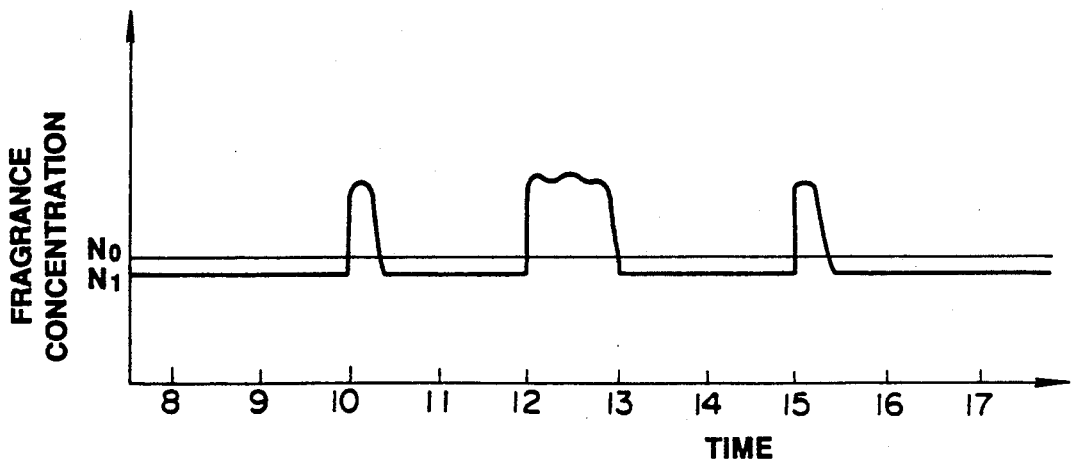

Table 1 shows an example of effects in response to the type of fragrance when the fragrant-air supplying apparatus 10 supplies fragrance-mixed air to the room. In this case air with a lemon type fragrance is intermittently supplied to the room throughout working hours as shown in FIG. 6, to give light stimulation to workers to get rid of drowsiness. While air with a rosemary type fragrance is supplied for break and lunch time as shown in FIG. 7, to give relaxation to workers. In FIG. 6 and FIG. 7, fragrance concentration $N_o$ is the minimum value at which humans can detect the fragrance, while fragrance concentration $N_1$ is the undetectable value which is less than the fragrance concentration $N_o$ so that humans cannot smell the fragrance during a predetermined period. Accordingly, fragrance concentrations $N_o$ and Nhd 1 are set during working hours, the fragrance concentration can be readily adjusted and immediately increased to the suitable thereof without a long wait.

TABLE 1

| — | Type of Fragrance | Effect |
|---|---|---|
| A | Lemon | Enhancement of awareness, light stimulation, and refreshment |
| B | Rosemary | Relaxation |

Accordingly, plural types of fragrant air can be supplied in response to a predetermined time interval in a day, so that the room atmosphere can be kept at the optimum conditions for work. In addition, fragrance-mixed air having physiological and psychological effects on the human body can be used so as to have a good physical and mental influence on the human body.

The above is a description of preferred embodiments of the present invention. This invention may be implemented in still other ways without departing from the spirit or essential character thereof. Therefore, the preferred embodiments described herein are illustrative and not restrictive, and the scope of the invention being indicated by the appended claims and all variations which come within the meaning of the claims are intended to be embraced therein.

What is claimed is:

1. A method for supplying fragrant air, the method comprising the steps of:

producing a mist containing fragrant material by blowing air into a liquid containing the fragrant material;

removing larger droplets from the mist; and extracting an evaporated fragrance containing air from the mist, entraining such air in a stream of conditioned air, and intermittently controlling the concentration of the evaporated fragrance between a value slightly less than the minimum detectable level and a value above said level at the distribution location of said condition air.

2. A method for supplying fragrant air according to claim 1 wherein the mist is blown onto a solid object to cohere the mist at the surface of the object.

3. A method for supplying fragrant air according to claim 1 wherein the evaporated fragrance containing air is combined with conditioning-air generated in an air conditioning system.

4. An apparatus for supplying fragrant air, the apparatus comprising:

fragrant-material supplying means;

mist-generating means for mixing a predetermined amount of fragrant material supplied from the fragrant-material supplying means with air which is supplied externally to form mist;

fragrant-air separating means for separting larger droplets from the mist by blowing the mist thereto;

fragrant-air introducing means comprising a plurality of holes located proximally the mist traveling direction of the evaporated fragrance containing air, so that the holes are offset from the fragrant-air separating means which is located down stream from the fragrant air introducing means;

air-supplying means for mixing the evaporated fragrance containing air introduced from the fragrant-air introducing means with conditioned-air supplied from an air conditioner to make fragrance-mixed air, and supplying the fragrance-mixed air to a predetermined space; and a controller for controlling the concentration of the evaporated fragrance containing air to be supplied to the predetermined space, the controller having fragrance concentration data for determining fragrance concentration in the predetermined space.

5. A method for supplying fragrant air according to claim 4 wherein said mist-generating means comprises ultrasonic-oscillating means and said fragrant-material supplying means to compose mist produced by vibration.

6. A method for supplying fragrant air according to claim 4 wherein said mist-generating means comprises compressed-air supplying means and said fragrant-material supplying means to compose mist produced by blowing compressed air to fragrant material.

7. A method for supplying fragrant air according to claim 4 wherein said fragrant-air separating means comprises mist-collided means, said mist-collided means is a surface portion being perpendicularly faced in response to the mist traveled direction to separate evaporated fragrant air from mist.

8. A method for supplying fragrant air according to claim 7 wherein said surface portion is concave, an inner surface of which is faced to the mist traveled direction.

9. A method for supplying fragrant air according to claim 7 wherein said surface portion has a barrier oppositely extended to the mist traveled direction.

10. A method for supplying fragrant air according to claim 7 wherein said surface portion has a barrier oppositely extended to the mist traveled direction.

11. A method for supplying fragrant air according to claim 7 wherein said surface portion is concave and has an inner surface facing towards the mist traveled direction.

12. A building having an apparatus for supplying fragrant air, wherein the building having an apparatus comprises:

fragrant-material supplying means;

mist-generating means for mixing a predetermined amount of fragrant material supplied from the fragrant-material supplying means with air which is supplied externally to form mist;

fragrant-air separating means for separting larger droplets from the mist by blowing the mist thereto;

fragrant-air introducing means comprising a plurality of holes located proximally the mist traveling direction of the evaporated fragrance containing air, so that the holes are offset from the fragrant-air separating means which is located down stream from the fragrant air introducing means;

air-supplying means for mixing the evaporated fragrance containing air introduced from the fragrant-air introducing means with conditioned-air supplied from an air conditioner to make fragrance-mixed air, and supplying the fragrance-mixed air to the rooms in the building through a distributing passage; and a controller for controlling the concentration of the evaporated fragrance containing air to be supplied to the predetermined space, the controller having fragrance concentration data for determining fragrance concentration in the predetermined space.

13. A building having an apparatus for supplying fragrant air according to claim 12 wherein the distributing passage is an air duct which extends from the air conditioner to distribute fragrance-mixed air to each room in the building.

14. A building having an apparatus for supplying fragrant air according to calim 12 wherein said mist-generating means comprises compressed-air supplying means and said fragrant-material supplying means to compose mist produced by blowing compressed air to fragrant material.

15. A building having an apparatus for supplying fragrant air according to calim 12 wherein said mist-generating means comprises ultrasonic-oscillating means and said fragrant-material supplying means to compose mist produced by vibration.

16. A building having an apparatus for supplying fragrant air according to calim 12 wherein said fragrant-air separating means comprises mist-collided means, said mist-collided means is a surface portion being perpendicularly faced in response to the mist traveled direction to separate evaporated fragrant air from mist.

17. A building having an apparatus for supplying fragrant air according to calim 12 wherein said surface portion has a barrier oppositely extended to the mist traveled direction.

18. A building having an apparatus for supplying fragrant air according to calim 16 wherein said surface portion is concave, an inner surface of which is faced to the mist traveled direction.

19. A building having an apparatus for supplying fragrant air according to claim 16 wherien said surface portion has a barrier oppositely extended to the mist traveled direction.

20. A building having an apparatus for supplying fragrant air according to claim 16 wherein said surface portion is concave and has an inner surface facing towards the mist traveled direction.

* * * * *